(12) United States Patent
Jamil et al.

(10) Patent No.: US 10,335,452 B2
(45) Date of Patent: Jul. 2, 2019

(54) METHOD OF TREATING PATIENTS WITH HEPATORENAL SYNDROME TYPE 1

(71) Applicant: Mallinckrodt Hospital Products IP Limited, Dublin (IE)

(72) Inventors: Khurram Jamil, Yardley, PA (US); Stephen Chris Pappas, The Woodlands, TX (US); Jim Potenziano, Binghamton, NY (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 531 days.

(21) Appl. No.: 14/920,392

(22) Filed: Oct. 22, 2015

(65) Prior Publication Data
US 2016/0113994 A1 Apr. 28, 2016

Related U.S. Application Data

(60) Provisional application No. 62/068,357, filed on Oct. 24, 2014, provisional application No. 62/151,384, filed on Apr. 22, 2015.

(51) Int. Cl.
| | | |
|---|---|---|
| *A61K 38/11* | (2006.01) | |
| *A61K 38/095* | (2019.01) | |
| *A61B 5/0205* | (2006.01) | |
| *A61B 5/145* | (2006.01) | |
| *A61K 9/00* | (2006.01) | |

(Continued)

(52) U.S. Cl.
CPC .......... *A61K 38/095* (2019.01); *A61B 5/0205* (2013.01); *A61B 5/14542* (2013.01); *A61K 9/0019* (2013.01); *A61K 38/38* (2013.01); *A61K 45/06* (2013.01); *A61M 27/002* (2013.01); *G01N 15/10* (2013.01); *G01N 33/4925* (2013.01); *G01N 2015/008* (2013.01); *G01N 2015/1062* (2013.01)

(58) Field of Classification Search
CPC ....... A61K 38/00; A61K 38/38; C07K 14/765
See application file for complete search history.

(56) References Cited

U.S. PATENT DOCUMENTS 7,160,853 B2 1/2007 Lebrec et al.
9,655,945 B2 5/2017 Angeli et al.
(Continued)

OTHER PUBLICATIONS

Dr. Alan W. Grogono. Base Excess & Calculated Bicarbonate. http://www-users.med.cornell.edu/~spon/picu/calc/basecalc.htm (Year: 2001).*

(Continued)

*Primary Examiner* — Marcela M Cordero Garcia
*Assistant Examiner* — Jia-Hai Lee

(57) ABSTRACT

The principles and embodiments of the present disclosure relate to methods for using terlipressin to treat a patient having impaired renal function associated with liver disease. A patient identified as suffering from HRS-1 is tested to determine if the patient meets at least two out of three criteria, wherein the three criteria include a WBC<4 or >12 cells/µL; HR>90 bpm; and any one of $HCO_3$<21 mmol/L or $PaCO_2$<32 mmHg or >20 breaths per minute. If the patient meets at least two of the criteria, he or she is administered terlipressin in an amount effective to produce a reduction in serum creatinine of at least 1.0 mg/dL.

28 Claims, 3 Drawing Sheets

| SIRS Subgroup (≥2 SIRS Criteria) vs. Non-SIRS Subgroup (<2 SIRS Criteria) | | | |
|---|---|---|---|
| | Terlipressin | Placebo | P-Value |
| *Confirmed HRS Reversal*, n / N (%) | | | |
| SIRS | 9 / 28 (32.1) | 1 / 30 (3.3) | 0.0048 |
| Non-SIRS | 10 / 69 (14.5) | 12 / 69 (17.4) | 0.8166 |
| *HRS Reversal*, n / N (%) | | | |
| SIRS | 12 / 28 (42.9) | 2 / 30 (6.7) | 0.0018 |
| Non-SIRS | 11 / 69 (15.9) | 13 / 69 (18.8) | 0.8227 |
| *Change from baseline to end of treatment in SCr mg/dL, with interaction* | | | |
| SIRS | -1.7 | -0.5 | <0.0001 (T vs. P, -1.3) |
| Non-SIRS (w/o interation) | N/C -0.8 | N/C -0.7 | N/C 0.4403 (T vs. P, -0.1) |
| *Overall Survival (survival estimate)* Alive at Day 90, n / N (%) | | | |
| SIRS | 0.571 16 / 28 (57.1) | 0.467 14 / 30 (46.7) | 0.5386 |
| Non-SIRS | 0.580 40 / 69 (58.0) | 0.569 40 / 69 (58.0) | 0.8581 |
| *Transplant-free Survival (survival estimate)* Alive and Transplant-free at Day 90, n / N (%) | | | |
| SIRS | 0.464 13 / 28 (46.4) | 0.233 7 / 30 (23.3) | 0.0760 |
| Non-SIRS | 0.245 17 / 69 (24.6) | 0.255 19 / 69 (27.5) | 0.5762 |

(51) Int. Cl.
| | |
|---|---|
| A61K 38/38 | (2006.01) |
| A61K 45/06 | (2006.01) |
| A61M 27/00 | (2006.01) |
| G01N 15/10 | (2006.01) |
| G01N 33/49 | (2006.01) |
| G01N 15/00 | (2006.01) |

(56) References Cited

U.S. PATENT DOCUMENTS

| | | | |
|---|---|---|---|
| 2004/0102362 | A1 | 5/2004 | Lebrec et al. |
| 2008/0058265 | A1* | 3/2008 | Rezaie .................. C12N 9/6464 514/1.4 |
| 2011/0237494 | A1 | 9/2011 | Laporte et al. |
| 2012/0157526 | A1 | 6/2012 | Jalan et al. |
| 2014/0378660 | A1 | 12/2014 | Short et al. |

OTHER PUBLICATIONS

Trzeciak et al. Inclusion Criteria for Clinical Trials in Sepsis*. CHEST 2005; 127:242-245. (Year: 2005).*
Martin-Llahi et al. Terlipressin and Albumin vs Albumin in Patients With Cirrhosis and Hepatorenal Syndrome: A Randomized Study. Gastroenterology 2008;134:1352-1359. (Year: 2008).*
Salerno et al. Diagnosis, prevention and treatment of hepatorenal syndrome in cirrhosis. Gut. Sep. 2007; 56(9):1310-8. (Year: 2007).*
EMC+, "Glypressin 0.12mg/ml Solution for Injection," retrieved from https://www.medicines.org.uk/emc/medicine/21750 (last updated on Apr. 23, 2013).
"Glypressin Solution for Injection," New Zealand Data Sheet, retrieved from http://www.medsafe.govt.nz/profs/datasheet/g/Glypressin01mgmlFerringinj.pdf (Apr. 21, 2015).
"Glypressin Solution for Injection," Product Information, retrieved from http://secure.healthlinks.net.au/content/ferring/pi.cfm?product=fppglyps20512 (retrieved on Dec. 23, 2015).
International Search Report and Written Opinion issued in PCT/US2015/056861 dated Feb. 9, 2016 (13 pages).
Maggio et al.,"Sepsis and Septic Shock—Critical Care Medicine—Merck Manuals Professional Edition," retrieved from http://www.merckmanuals.com/professional/critical-care-medicine/sepsis-and-septic-shock/sepsis-and-septic shock (Jul. 1, 2013).
Krag et al., "Efficacy and safety of terlipressin in cirrhotic patients with variceal bleeding or hepatorenal syndrome," Adv Ther., 25(11):1105-1140 (2008) Abstract Only.
Rodriguez et al., "Terlipressin and albumin for type-1 hepatorenal syndrome associated with sepsis," Journal of Hepatology, 60(5):955-961 (2014).
Salerno et al., "Diagnosis, Preventions and Treatment of Hepatorenal Syndrome in Cirrhosis," Gut., 56:1310-1318 (2007).
Thabut et al., "Model for end-stage liver disease score and systemic inflammatory response are major prognostic factors in patients with cirrhosis and acute functional renal failure," Hepatology, vol. 46(6):1872-1882 (2007) Abstract Only.
Sanyal et al., "A Randomized, Prospective, Double-Blind, Placebo-Controlled Trial of Terlipressin for Type 1 Hepatorenal Syndrome, " Gastroenterology, 134(5):1360-1368 (2008).

Wong et al., "G14: Systemic inflammatory response syndrome (SIRS) is a major determinant of treatment response to terlipressin for hepatorenal syndrome type 1 (HRS-1)," Journal of Hepatology, 62:S235-S236 (2015).
Angeli, P., Terlipressin for the treatment of hepatorenal syndrome in patients with cirrhosis, Expert Opinion on Orphan Drugs, 2013, vol. 1, No. 3, pp. 241-248.
Boyer, T.D. et al., A randomized, placebo-controlled, double-blind study to confirm the reversal of hepatorenal syndrome type I with terlipressin: the Reverse trial design, Open Access Journal of Clinical Trails, 2012, vol. 4, pp. 39-49.
Caraceni, P. et al., Long-term treatment of hepatorenal syndrome as a bridge to a liver transplantation, Digestive and Liver Disease, 2011, vol. 43, pp. 242-245.
Cavallin, M. et al., Terlipressin Given by Continuous Intravenous Infusion Versus Intravenous Boluses in the Treatment of Hepatorenal Syndrome: A Randomized Controlled Study, 2016, vol. 63, No. 3, pp. 983-992.
Fimiani, B. et al., The use of terlipressin in cirrhotic patients with refractory ascites and normal renal function: A multicentric study, European Journal of Internal Medicine, 2011, 4 pages.
Gerbes, A.L. et al., Correspondence (Letter to Editor) Terlipressin for Hepatorenal Syndrome: Continuous Infusion as an Alternative to IV Bolus Administration, Gastroenterology, 2009, vol. 137, pp. 1179-1189.
Gow, P.J. et al., Outpatient Terlipressin Infusion for the Treatment of Refractory Ascites, Letters to the Editor, The AMerican Journal of Gastroenterology, 2016, pp. 1041-1042.
Hsu, S.J. and Huang, H.C., Management of ascites in patients with liver cirrhosis: Recent evidence and controversies, Journal of the Chinese Medical Association, 2013, vol. 76, pp. 123-130.
Kalambokis, G.N. and Tsianos, E.V., Correspondence (Letter to Editor) Vasoconstrictor Therapy for Patients with Cirrhosis with Ascites but Without Hepatorenal Syndrome, American Assoication for the Study of Liver Diseases, 2008, p. 686.
Krag, A. et al., Terlipressin Improves Renal Function in Patients with Cirrhosis and Ascites Without Hepatorenal Syndrome, Hepatology, 2007, vol. 46, No. 6, pp. 1863-1871.
Pharmain, Press Release—FDA Grants OrphanDrug Designation for Novel Terlipressin Formulation for the Treatment of Ascites, http://pharmain.com/fdagrantsorphandrugdesignationfornovelterlipressinformulationforthetreatmentofascites/, Apr. 23, 2017, 2 pages.
Piano, S. et al., Continuous recurrence of type 1 hepatorenal syndrome and long-term treatment with terlipressin and albumin: A new exception to MELD score in the allocation system to liver transplantation?, Journal of Hepatology, 2011, vol. 55, pp. 491-496.
Robertson, M. et al., Continuous Outpatient Terlipressin Infusion for Hepatorenal Syndrome as a Bridge to Successful Liver Transplantation, Hepatology, 2014, pp. 2125-2126.
Testro, A.G. et al., Long-term outcome of patients treated with terlipressin for types 1 and 2 hepatorenal syndrome, Hepatology, 2007, vol. 23, pp. 1535-1540.
Wong, F. et al., Effects of a selective vasopressin V2 receptor antagonist, satavaptan, on ascites recurrence after paracentesis in patients with cirrhosis, Journal of Hepatology, 2010, vol. 53, pp. 283-290.
Wong, F. et al., Working Party proposal for a revised classification system of renal dysfunction in patients with cirrhosis, Gut, 2011, vol. 60, pp. 702-709.

* cited by examiner

FIG. 3

SIRS Subgroup (≥2 SIRS Criteria) vs. Non-SIRS Subgroup (<2 SIRS Criteria)

|  | Terlipressin | Placebo | P-Value |
|---|---|---|---|
| *Confirmed HRS Reversal,* n / N (%) | | | |
| SIRS | 9 / 28 (32.1) | 1 / 30 (3.3) | 0.0048 |
| Non-SIRS | 10 / 69 (14.5) | 12 / 69 (17.4) | 0.8166 |
| *HRS Reversal,* n / N (%) | | | |
| SIRS | 12 / 28 (42.9) | 2 / 30 (6.7) | 0.0018 |
| Non-SIRS | 11 / 69 (15.9) | 13 / 69 (18.8) | 0.8227 |
| *Change from baseline to end of treatment in SCr* mg/dL, with interaction | | | |
| SIRS | -1.7 | -0.5 | <0.0001 (T vs. P, -1.3) |
| Non-SIRS (w/o interation) | N/C -0.8 | N/C -0.7 | N/C 0.4403 (T vs. P, -0.1) |
| *Overall Survival (survival estimate)* Alive at Day 90, n / N (%) | | | |
| SIRS | 0.571 16 / 28 (57.1) | 0.467 14 / 30 (46.7) | 0.5386 |
| Non-SIRS | 0.580 40 / 69 (58.0) | 0.569 40 / 69 (58.0) | 0.8581 |
| *Transplant-free Survival (survival estimate)* Alive and Transplant-free at Day 90, n / N (%) | | | |
| SIRS | 0.464 13 / 28 (46.4) | 0.233 7 / 30 (23.3) | 0.0760 |
| Non-SIRS | 0.245 17 / 69 (24.6) | 0.255 19 / 69 (27.5) | 0.5762 |

METHOD OF TREATING PATIENTS WITH HEPATORENAL SYNDROME TYPE 1

CLAIM OF PRIORITY

This application claims priority under 35 USC § 119(e) to U.S. Patent Application Ser. No. 62/151,384, filed on Apr. 22, 2015, and U.S. Patent Application Ser. No. 62/068,357, filed on Oct. 24, 2014, the entire contents of which are hereby incorporated by reference.

TECHNICAL FIELD

Principles and embodiments of the present disclosure relate generally to methods of treating patients with type-1 hepatorenal syndrome.

BACKGROUND

Hepatorenal Syndrome Type-1 (HRS Type 1 or HRS-1) is the development of acute kidney failure in patients with late-stage liver cirrhosis in the absence of any other cause. It is characterized by rapid onset of renal failure with a high mortality rate that exceeds 80% with within three months. Renal failure is an identified complication of cirrhosis of the liver; and, acute renal failure is known to have poor prognosis for patients with cirrhosis of the liver. In various instances, the renal failure may be caused by hypovolemia, hepatorenal syndrome without ongoing infection, or hepatorenal syndrome with an ongoing infection. Unfortunately, patients with HRS Type-1 may die from renal failure while waiting for a liver transplant. Currently, there is no way of determining which patients could maximally benefit from terlipressin treatment to reverse HRS Type-1.

Hepatorenal Syndrome (HRS) is indicated by low glomerular filtration rate due to renal vasoconstriction, splanchnic and peripheral arterial vasodilatation producing decreased vascular resistance, and portal hypertension. HRS is indicated by cirrhosis with ascites, serum levels of creatinine>133 µmol/l (1.5 mg/dL), no improvement of serum levels of creatinine (decrease to a level of ≤133 µmol/l) after at least 2 days of diuretic withdrawal and volume expansion with albumin, and the absence of shock and parenchymal kidney disease. HRS Type 1 is indicated by doubling of the initial serum levels of creatinine to >226 µmol/l (2.56 mg/dL) in <2 weeks.

Normal creatinine levels range from 0.7 to 1.3 mg/dL in men and 0.6 to 1.1 mg/dL in women. One mg/dl of creatinine equals 88.4 µmol/l.

Certain mechanisms that work to maintain effective arterial blood volume and relatively normal arterial pressure in patients with cirrhosis, however, affect kidney function, such as sodium and solute-free water retention, which can lead to ascites and edema, and to renal failure by causing intrarenal vasoconstriction and hypoperfusion. Acites can result from the combination of portal hypertension and splanchnic arterial vasodilation that alters intestinal capillary pressure and permeability, which facilitates the accumulation of the retained fluid in the abdominal cavity.

A factor contributing to ascites formation is a splanchnic vasodilation that results in a decreased effective arterial blood volume. Portal hypertension also results from increased hepatic resistance to portal blood flow in cirrhotic livers, and may induce splanchnic vasodilation. There may be a marked impairment in solute-free renal water excretion and renal vasoconstriction, which leads to HRS.

In various instances, there may be signs of hepatic decompensation including INR>1.5, ascites, and encephalopathy. Hyponatremia is also a frequent complication of patients with cirrhosis and ascites that is associated with increased morbidity.

Systemic Inflammatory Response Syndrome (SIRS) is an inflammatory response that is not necessarily related to an infection, but may be due to nonspecific insults that initially produces local cytokines. SIRS is typically characterized by four criteria, including (1) core body temperature of less than 36° C. (96.8° F.) or greater than 38° C. (100.4° F.), (2) a heart rate of greater than 90 beats per minute, (3) tachypnea (high respiratory rate), with greater than 20 breaths per minute; or, an arterial partial pressure of carbon dioxide ($CO2$) of less than 4.3 kPa (32 mmHg), and (4) a white blood cell count less than 4000 cells/mm$^3$ (4×109 cells/L) or greater than 12,000 cells/mm$^3$ (12×109 cells/L); or the presence of greater than 10% immature neutrophils (band forms) band forms greater than 3% is called bandemia or a "left-shift." SIRS can be diagnosed when two or more of these criteria are present.

Sepsis has been defined as a systemic inflammatory response to infection, and septic shock is sepsis complicated by either hypotension that is refractory to fluid resuscitation or by hyperlactatemia.

The mortality of patients suffering from HRS and SIRS can be quite high, approaching 70%.

A number of studies have been conducted on patients having end-stage liver disease and systemic inflammatory responses. One such study described by Thabut et al., disclosed in HEPATOLOGY, Vol. 46, No. 6, 2007 entitled "Model for End-Stage Liver Disease Score and Systemic Inflammatory Response Are Major Prognostic Factors in Patients with Cirrhosis and Acute Functional Renal Failure", which is incorporated herein by reference in its entirety, concluded that the presence of SIRS criteria with or without infection was a major independent prognostic factor in patients with cirrhosis and acute functional renal failure.

The presence of HRS and SIRS typically indicates a short life span if not effectively treated with the proper medication within a short span of time. It is therefore paramount that the most effective treatments for patients presenting with particular symptoms be identified and the patients started on an appropriate regimen as quickly as possible.

Terlipressin is a synthetic analogue of vasopressin having a prolonged effect, which acts as a peptidic vasopressin V1a receptor agonist. Terlipressin is a derivative of vasotocin prepared by extending the N-terminal by three amino acid residues, and used as a vasoactive drug in the management of hypotension. Terlipressin may be synthesized by coupling amino acids stepwise to one another in a liquid or solid phase with a peptide synthesizer. Terlipressin is a prodrug that slowly metabolizes to lysine-vasopressin and in this way provides prolonged biological effect. The half-life of terlipressin is 6 hours (the duration of action is 2-10 hr), as opposed to the short half-life of vasopressin, which is only 6 minutes (the duration of action is 30-60 min).

The chemical structure for terlipressin in an injectable formulation is show below.

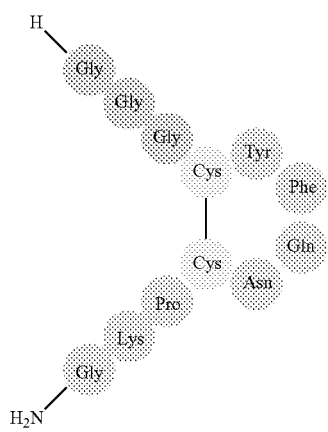

Molecular Formula: $C_{52}H_{74}N_{16}O_{15}S_2$
Molecular Weight: 1227.4 daltons
Appearance: Homogenous lyophilized white to off-white solid
Solubility: Clear, colorless solution in saline
Vials: Colorless glass vials containing 11 mg of a white to off-white solid, 1 mg active ingredient and 10 mg mannitol.

The active ingredient, N—[N—(N-glycylglycyl)glycyl]-8-L-lysinevasopressin, is a synthetically manufactured hormonogen of 8-lysine vasopressin, composed of 12 amino acids and having the characteristic ring structure of a cyclic nonapeptide with a disulfide bridge between the fourth and the ninth amino acid. Three glycyl-amino acids are substituted at position 1 (cysteine) of 8-lysine-vasopressin. By this N-terminal extension of 8-lysine-vasopressin the metabolic degradation rate of the active ingredient is significantly reduced, because the glycyl molecules inhibit rapid N-terminal enzymatic degradation.

SUMMARY

The present invention avoids the unnecessary administration of drug to patients who are critically ill because of the surprising discovery that terlipressin is very effective in patients exhibiting certain criteria but is not effective in patients that do not meet this criteria. As with most medication, side effects and complications may be a problem. Possible warnings and precautions associated with terlipressin include ischemia. Ischemic events (cardiac, gastrointestinal, and skin) can occur following administration of terlipressin and may require temporary interruption, dose decrease, or permanent discontinuation. Manifestations may include angina, ECG changes, severe abdominal pain with GI bleeding, peripheral cyanosis and extremity pain. Further, due to its constrictive effects on smooth muscle, terlipressin should be used with caution in patients with severe asthma or chronic obstructive pulmonary disease (COPD). Patients with these disorders who receive terlipressin should be closely monitored and any bronchospasm should be treated symptomatically. Also, terlipressin may cause fetal harm when administered to a pregnant woman, since it causes significant increases in uterine activity and reduction in endometrial blood flow. Since patients with HRS-1 are critically ill and terlipressin can have side-effects, to determine if a patient is likely to respond to terlipressin and only treating those patients can be extremely beneficial and even life-saving as terlipressin is known to be effective in 33-60% of HRS-1 patients. (See Krag et al. Adv Ther. 2008; 25(11):1105-1140). Adverse reaction in more than 10% patients included vomiting, abdominal pain, nausea, diarrhea, intestinal ischemia, dyspnea, sneezing, pulmonary edema and fluid overload. All conditions that could be severely detrimental to already fragile patients with HRS-1.

Principles and embodiments of the present disclosure relate generally to methods of treating patients having HRS-1 by administering terlipressin to the patients to obtain reversal of the HRS-1. In one or more embodiments, response criteria provide a new and useful function of indicating a likelihood of improved response by a patient to the administration of terlipressin.

Some aspects of the disclosure relate to a method of treating HRS-1, where the method includes identifying a plurality of patients as having HRS-1; determining that a first patient of the plurality exhibits at least two of the following three criteria:

(i) a white blood cell count (WBC) less than 4,000 cells/mm$^3$ or greater than 12,000 cells/mm$^3$,
(ii) a heart rate of greater than 90 beats per minute (BPM), and
(iii) either a partial pressure of carbon dioxide in the blood (PaCO2)<32 mmHg or a blood bicarbonate (HCO3) level<23 mmol/L;

determining that, because the first patient exhibits at least two of the three criteria, the HRS-1 of the first patient is likely to respond to treatment with terlipressin; administering to the first patient an amount of terlipressin effective to treat HRS-1 in the first patient; determining that a second patient of the plurality exhibits only one or none of the three criteria; determining that, because the second patient does not exhibit at least two of the three criteria, the HRS-1 of the second patient is unlikely to respond to treatment with terlipressin; and excluding the second patient from treatment with terlipressin.

In various embodiments, a treatment other than terlipressin is administered to the second patient.

In various embodiments, criterion (iii) is a HCO3 level of <23 mmol/L; it may alternatively be a HCO3 level of <21 mmol/L.

In various embodiments, the dosage of terlipressin is in the range of 2.0 mg to 12.0 mg per day for 1 to 28 days; the method may also include determining if the first patient has a reduction in serum creatinine (SCr) level during the 1 to 28 days of terlipressin administration.

In various embodiments, the amount of terlipressin administered to the first patient is in the range of about 0.5 mg to about 2.0 mg every 4 to 6 hours. In some embodiments, the terlipressin is administered as a single dose once every 4 to 6 hours.

In various embodiments, the method of treating HRS-1 in a patient further comprises determining if the first patient has a reduction in serum creatinine (SCr) level during the initial 1 to 4 days of terlipressin administration.

In various embodiments, the method of treating HRS-1 in a patient further comprises discontinuing administration of terlipressin to the first patient if the first patient does not show a reduction in SCr level during the initial 1 to 4 days of treatment.

In various embodiments, the method of treating HRS-1 in a patient further comprises continuing administration of terlipressin to the first patient for an additional 3 to 12 days if the first patient shows a reduction in SCr level during the initial 1 to 4 days.

In various embodiments, the administration of terlipressin to the first patient produces a reversal of the HRS-1, defined as a decrease in SCr level to ≤1.5 mg/dl.

In various embodiments, the method of treating RS-1 in a patient further comprises treating the identified patient with up to a maximum of 100 g per day of albumin for each day of the time period that the patient is administered terlipressin.

In various embodiments, HRS-1 patients who are excluded from treatment with terlipressin, or in whom terlipressin treatment is discontinued, may be treated with one or more other pharmacological agents such as norepinephrine, vasopressin, or a combination of midodrine and octreotide. A number of experimental agents have shown some effect in improving kidney function in patients with HRS. These include N-acetylcysteine, misoprostol (a synthetic analogue of prostaglandin E1 and a renal vasodilator), and an (ET) a endothelin receptor antagonist, BQ123, which is a cyclic peptide consisting of five amino acids in the following sequence: D-tryptamine-D-aspartic acid-L-proline-D-valine-L-leucine. Another option is transjugular intrahepatic portosystemic shunt (TIPS), a self-expandable metal stent inserted into a hepatic blood vessel to divert blood flow and hence reduce portal pressure. Renal support in the form of dialysis is commonly instituted to manage acute fluid overload in HRS-1 patients, particularly if pharmacological therapies fail. The only effective and permanent treatment for end-stage cirrhosis and HRS is liver transplantation.

Aspects of the present disclosure relate to a method of increasing the effectiveness of terlipressin for the treatment of impaired renal function associated with liver disease, comprising: identifying a plurality of patients with end-stage liver disease and impaired renal function; testing the plurality of patients to determine whether each meets each of the following three criteria (i)-(iii):
  (i) a white blood cell count either less than 4,000 cells/mm$^3$ or greater than 12,000 cells/mm$^3$,
  (ii) a heart rate of greater than 90 beats per minute, and
  (iii) either (a) a PaCO2 of <32 mmHg or (b) a HCO3 level of <23 mmol/L or (c) tachypnea with more than 20 breaths per minute;
determining that a first patient of the plurality meets at least two of the three criteria; determining that, because the first patient meets at least two of the three criteria, the first patient's renal function is more likely to improve upon treatment with terlipressin than if the first patient exhibited only one or none of the three criteria; administering to the first patient an amount of terlipressin effective to improve the first patient's renal function; determining that a second patient of the plurality meets only one or none of the three criteria; determining that, because the second patient does not meet at least two of the three criteria, the second patient's renal function is less likely to respond to treatment with terlipressin than if the second patient exhibited at least two of the three criteria; and excluding the second patient from treatment with terlipressin.

In various embodiments, the plurality of patients are identified as having cirrhosis of the liver; in some of those embodiments, the patients are also identified as having a Child-Pugh score of B or C.

In various embodiments, during treatment with terlipressin the first patient is tested to determine if the first patient's renal function is improved compared to that patient's renal function prior to treatment with terlipressin.

In various embodiments, criterion (iii) is a HCO3 level of <23 mmol/L; it may alternatively be a HCO3 level of <21 mmol/L.

In various embodiments, the method of increasing the effectiveness of terlipressin further comprises determining that a third patient of the plurality has overt sepsis, septic shock, or uncontrolled infection, and excluding the third patient from the administration of terlipressin because of the presence of overt sepsis, septic shock, or uncontrolled infection.

In various embodiments, the method includes determining that the plurality of patients have cirrhosis of the liver with a Child-Pugh score of B or C.

In various embodiments, the dosage of terlipressin administered to the first patient over a 4 hour to 6 hour period is in the range of 0.5 mg to about 2.0 mg.

In various embodiments, the terlipressin is administered to the first patient as a continuous IV drip.

In various embodiments, the dosage of terlipressin administered to the first patient does not exceed 4.0 mg over each 24 hour period of administration.

In various embodiments, the method of increasing the efficacy of terlipressin further comprises determining a baseline serum creatinine level for the first patient within 2 days prior to starting the administration of terlipressin to the first patient and testing the first patient at least once within four days after starting the administration of terlipressin to determine if the first patient's serum creatinine level has decreased compared to the baseline level.

In various embodiments, the administration of terlipressin to the first patient is continued if testing the first patient's serum creatinine level after starting the administration of terlipressin shows that the first patient's serum creatinine level has decreased compared to the baseline level, and the administration is discontinued if the patient does not exhibit a decrease in the serum creatinine level.

In various embodiments, the first patient's serum creatinine level is shown to have decreased compared to the baseline level, and then administration of terlipressin to the patient is continued for an additional 3 days to 12 days (e.g., 3 to 8 days). In various embodiments, the serum creatinine level is tested and shown to have decreased to <1.5 mg/dL. In various embodiments, administration of terlipressin to the patient may be continued until at least one SCr value of <1.5 mg/dL is obtained. In various embodiments, the duration of treatment may be extend to a maximum of 15 days or 16 days if HRS reversal was first achieved on days 13 or 14, respectively.

Aspects of the present disclosure relate to a method for treating HRS-1, the method comprising: diagnosing a plurality of patients as having HRS-1; determining that a first and a second patient of the plurality do not have overt sepsis, septic shock, or uncontrolled infection; testing the first and second patients to determine whether each meets each of the following three criteria (i)-(iii):
  (i) a white blood cell count either less than 4,000 cells/mm$^3$ or greater than 12,000 cells/mm$^3$,
  (ii) a heart rate of greater than 90 beats per minute, and
  (iii) either (a) a partial pressure of carbon dioxide in the blood (PaCO2) of <32 mmHg or (b) a blood bicarbonate (HCO3) level of <23 mmol/L or (c) tachypnea with more than 20 breaths per minute;
determining that the first patient meets at least two of the three criteria; determining that, because the first patient meets at least two of the three criteria, the first patient's renal function is more likely to improve upon treatment with terlipressin than if the first patient exhibited only one or none of the three criteria; initiating administration of terlipressin to the first patient within two days of the determination that the first patient meets at least two of the three criteria, wherein the terlipressin is administered as an IV in an amount effective to reduce the first patient's serum creatinine level by at least 1.0 mg/dL; determining that the second patient meets only one or none of the three criteria; determining that, because the second patient does not meet at least two of the three criteria, the second patient's renal function is less likely to respond to treatment with terlipressin than if the second patient exhibited at least two of the three criteria; and excluding the second patient from treatment with terlipressin.

In various embodiments, a treatment other than terlipressin is administered to the second patient. The second patient may be treated with, for example, one or more of norepinephrine, vasopressin, or a combination of midodrine and octreotide, and/or may be given a transjugular intrahepatic portosystemic shunt. Alternatively or in addition, the second patient is in some embodiments treated with kidney dialysis.

In various embodiments, criterion (iii) is a HCO3 level of <23 mmol/L; it may alternatively be a HCO3 level of <21 mmol/L.

In various embodiments, the first patient is administered terlipressin as an IV every 4 to 6 hours for 16 days.

In various embodiments, the administration of terlipressin can be in a bolus or slow IV injection. In one embodiment, methods of treating a patient with HRS type-1 with the disclosed invention can be repeated one or more times or as necessary. In one aspect, if HRS type 1 recurs after discontinuation of initial treatment, terlipressin may be re-administered using the same dosing regimen for up to an additional 1 day, 2 days, 3 days, 4 days 5 days, 6 days, one week, two weeks, or three weeks. In another aspect, terlipressin can be discontinued 2 days following HRS-1 reversal or when a serum creatinine level≤1.5 mg/dL is first reached.

Aspects of the present disclosure relate to a method of identifying a subset of HRS-1 patients with an increased likelihood of responding to treatment with terlipressin compared to other HRS-1 patients, the method comprising: identifying a plurality of patients who have HRS-1 and who do not have overt sepsis, septic shock, or uncontrolled infection; for each patient of the plurality, measuring at least two of the following three variables (a)-(c):
  variable (a): white blood cell count;
  variable (b): number of heart beats per minute;
  variable (c): either blood HCO3 level or PaCO2 level or breaths per minute;
  within the plurality of patients, identifying a subset comprising one or more patients, all of whom meet at least two of the following three criteria (i)-(iii):
    (i) a white blood cell count either less than 4,000 cells/mm$^3$ or greater than 12,000 cells/mm$^3$,
    (ii) a heart rate of greater than 90 beats per minute, and
    (iii) either HCO3<23 mmol/L or PaCO2<32 mmHg or >20 breaths per minute,
wherein other patients of the plurality meet only one or none of the three criteria, so are not in the subset; and determining that the one or more patients in the subset have an increased likelihood of responding to treatment with terlipressin compared to the other patients of the plurality who are not in the subset.

In various embodiments, the method of identifying an HRS-1 patient with an increased likelihood of responding to terlipressin further comprises treating at least one patient of the subset with terlipressin; measuring the at least one patient's serum creatinine level after treatment has begun; and observing that the serum creatinine level in the blood of the at least one patient decreased upon treatment with terlipressin.

In various embodiments, patients of the plurality who meet only one or none of the three criteria are not in the subset and are excluded from terlipressin treatment.

In various embodiments, criterion (iii) is a HCO3 level of <23 mmol/L; it may alternatively be a HCO3 level of <21 mmol/L.

Another aspect of the present disclosure relates to the use of terlipressin for the treatment of HRS-1 in a patient meeting two or more of the following three criteria (i)-(iii):
  (i) a white blood cell count either less than 4,000 cells/mm$^3$ or greater than 12,000 cells/mm$^3$,
  (ii) a heart rate of greater than 90 beats per minute, and
  (iii) either HCO3<23 mmol/L or PaCO2<32 mmHg or >20 breaths per minute,
wherein the amount of terlipressin used is effective to produce a reduction in serum creatinine of at least 25% compared to baseline, reversal of HRS, and/or confirmed HRS reversal.

Another aspect of the present disclosure relates to a method of distributing a pharmaceutical product, the method comprising supplying terlipressin to a medical provider responsible for treating a patient suffering from type 1 hepatorenal syndrome, providing a recommendation to the medical provider to treat a patient who (a) is suffering from type 1 hepatorenal syndrome, (b) does not have overt sepsis, septic shock, or uncontrolled infection, and (c) meets two or more of the following three criteria (i)-(iii):
  (i) a white blood cell count either less than 4,000 cells/mm$^3$ or greater than 12,000 cells/mm$^3$,
  (ii) a heart rate of greater than 90 beats per minute, and
  (iii) either HCO3<23 mmol/L or PaCO2<32 mmHg or >20 breaths per minute,
with terlipressin in an amount effective to reduce the patient's serum creatinine level.

BRIEF DESCRIPTION OF THE DRAWINGS

Further features of embodiment of the present disclosure, their nature and various advantages will become more apparent upon consideration of the following detailed description, taken in conjunction with the accompanying drawings, which are also illustrative of the best mode contemplated by the applicants, and in which like reference characters refer to like parts throughout, where:

FIG. 3 illustrates a set of unexpected results from an exemplary embodiment of a terlipressin treatment protocol.

DETAILED DESCRIPTION

Figure 1:
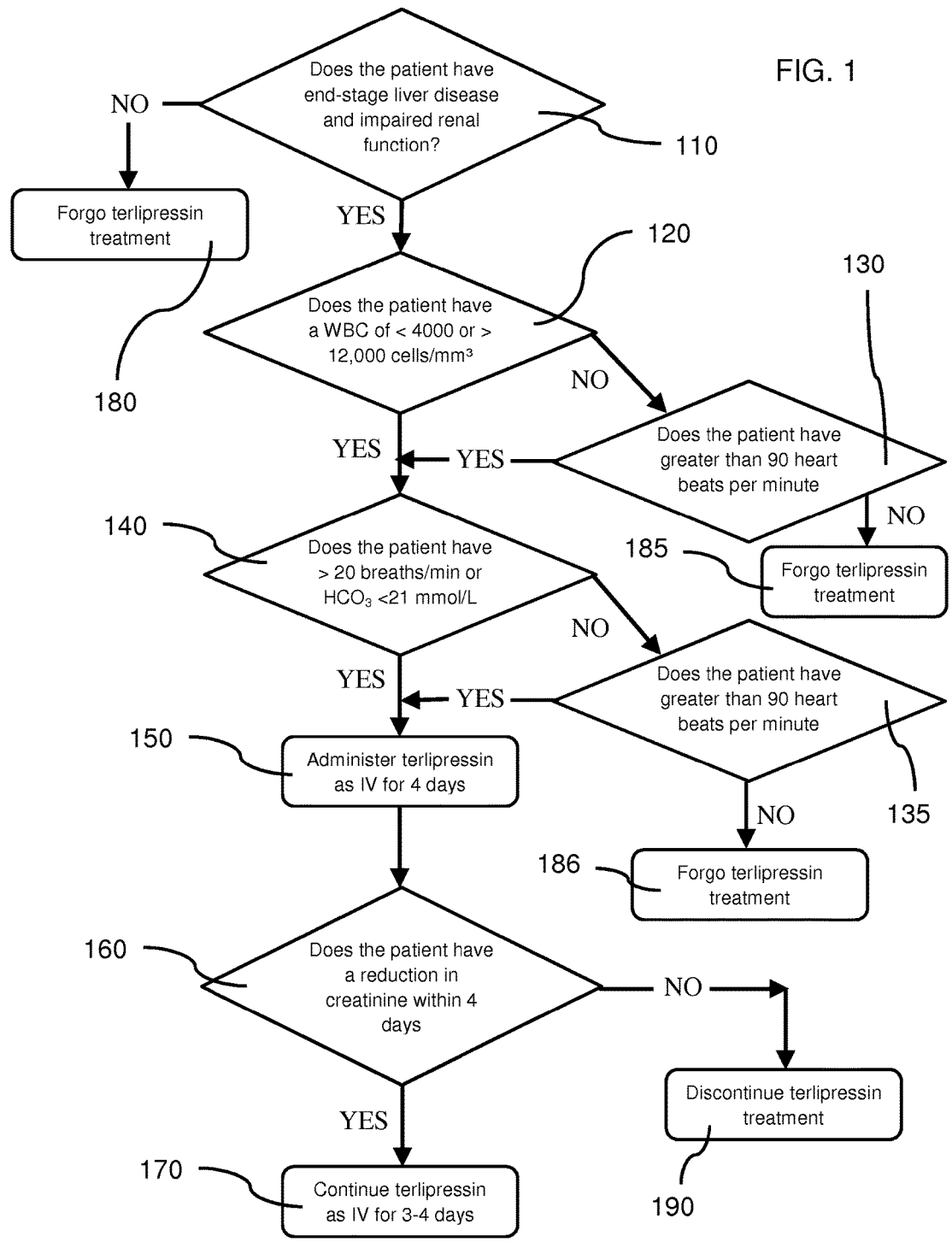
FIG. 1 illustrates an exemplary embodiment of a terlipressin treatment protocol.

The principles and embodiments of the present disclosure relate to methods of improving a patient's renal condition involving a treatment protocol comprising terlipressin. Accordingly, various embodiments of the present disclosure provide methods of treating a patient with terlipressin or terlipressin and albumin.

In embodiments of the present disclosure, the patient is evaluated to determine the particular disease and/or syndrome he or she may be suffering from, and beginning a treatment regimen for patients that will benefit from the administration of terlipressin.

In various embodiments, the patient has end stage liver disease complicated with acute kidney failure, such as HRS, and is treated with terlipressin.

In various embodiments, end-stage liver disease may be cirrhosis of the liver or fulminant liver failure. In various embodiments, the end-stage liver disease is complicated by impaired renal function.

An aspect of the present disclosure relates to a method of diagnosis of patients that show improved response to terlipressin treatment, as indicated by an increased probability of HRS reversal.

In one or more embodiments, the method of identifying an HRS-1 patient with an increased likelihood of responding to terlipressin treatment regimen comprises identifying a patient as having end stage live disease and impaired renal function, determining if the patient also exhibits at least two out of three criteria for SIRS, wherein the three response criteria include (1) a white blood cell count (WBC) that is less than 4,000 cells/mm$^3$ or greater than 12,000 cells/mm$^3$, (2) a heart rate of greater than 90 beats per minute (BPM), and (3) an HCO3<21 mmol/L, where HCO3 is considered a surrogate measurement that approximates the response criteria of arterial partial pressure of carbon dioxide (PaCO2) <32 mmHg. In various embodiments, a heart rate of >85 BPM and/or an HCO3<23 mmol/L may be applied as the response criteria.

An aspect of the present disclosure relates to terlipressin for use in the treatment of HRS-1 in a subject that is also exhibiting at least two of the following three response criteria:
(a) a white blood cell count (WBC) is less than 4,000 cells/mm$^3$ or greater than 12,000 cells/mm$^3$,
(b) a heart rate of greater than 90 beats per minute (BPM), and
(c) an HCO3<21 mmol/L, where HCO3 is considered a surrogate measurement that approximates the response criteria of arterial partial pressure of carbon dioxide (PaCO2) <32 mmHg. In various embodiments, one or more single dosages of terlipressin is administered to the subject, thereby treating the HRS-1.

In various embodiments, the terlipressin dosage is administered to the patient in the range of about 0.5 mg to about 2.0 mg every 4 to 6 hours, as a series of single doses, so that the patient receives a single dose in the range of about 0.5 mg to about 2.0 mg of terlipressin followed by another single dose 4 to 6 hours later. In various embodiments, a patient may receive 4 to 6 doses over a 24 hour period, where each dose is in the range of about 0.5 mg to about 2.0 mg. In various embodiments, the total dosage does not exceed 4.0 mg over a 24 hour period.

As shown in FIG. 1, an exemplary embodiment of a method of treating a patient via an embodiment of a terlipressin treatment protocol.

In various embodiments, a patient, who is initially identified as having end stage liver disease, for which treatment with a vasodilator may provide an improvement in renal function, is tested to determine the extent of the patient's cirrhosis and renal failure.

At 110, a patient is initially identified as having end stage live disease and impaired renal function. In various embodiments, a patient may be suffering from cirrhosis of the liver or fulminant liver failure, where a patient identified with cirrhosis of the liver may have a Child-Pugh score of A, B, or C. In various embodiments, a patient identified with cirrhosis of the liver that has a Child-Pugh score of B or C may be considered a viable candidate for terlipressin treatment. In various embodiments, a patient identified with cirrhosis of the liver that has a Child-Pugh score of C may be considered a viable candidate for terlipressin treatment.

[0062] Various complications of end-stage liver disease, and in particular cirrhosis, are recognized and have a notably poor prognosis.

In one or more embodiments, a treatment protocol comprising dosages of terlipressin surprisingly provides reversal of one or more complicating factors, such as vasodilation, and reduces mortality from the associated complications within a 90 day window starting with treatment.

In one or more embodiments, the terlipressin treatment protocol comprises identifying a patient having end-stage liver disease and impaired renal function, where the identified patient may benefit from a treatment comprising administration of terlipressin, determining if the patient also exhibits at least two out of three response criteria, and initiating terlipressin treatment by administering a daily dosage of terlipressin to the patient in an amount effective to produce an improvement in renal function, wherein an improvement in renal function is indicated by a reduction in SCr of at least 25% from baseline, reversal of HRS (defined as a decrease in SCr level to ≤1.5 mg/dl), and/or confirmed HRS reversal (defined as two serum creatinine values of ≤1.5 mg/dL at least 48 hours apart)).

In one or more embodiments, the terlipressin dosage may be in the range of about mg to about 10 mg, or 0.5 mg to about 5.0 mg, or 0.5 mg to about 2.0 mg, or 0.5 mg to about mg, or about 1.0 mg to about 2.0 mg per single administration. In various embodiments, the injections may be administered intravenously as slow bolus injections over 2 minutes, where the dose may be repeated every four to six hours. If on day 4 of therapy (after a minimum of 10 doses), SCr had decreased, but by less than 30% from the baseline value, the dose may be increased to 2 mg every 6 hours (±30 min) (8 mg/day). The dose may not be increased if the subject had coronary artery disease; or in the clinical setting of circulatory overload, pulmonary edema, or treatment-refractory bronchospasm. In various embodiments, if dosing was interrupted due to a non-ischemic adverse event, terlipressin may be restarted at the same or lower dose (i.e., 0.5 to 1 mg q6h).

At 180, a patient that is not diagnosed with an end-stage liver disease and impairment of renal function is excluded from the terlipressin treatment.

In one or more embodiments, the patient is tested for three specific response criteria, where the criteria include a determination of (1) whether the white blood cell count (WBC) is less than 4,000 cells/mm$^3$ or greater than 12,000 cells/mm$^3$, (2) whether the patient has a heart rate of greater than 90 beats per minute (BPM), and/or (3) whether the patient has tachypnea with greater than 20 breaths per minute or an HCO3<21 mmol/L, where HCO3 is considered a surrogate measurement that approximates the response criteria of arterial partial pressure of carbon dioxide (PaCO2)<32 mmHg. In various embodiments, the response criterion of a patient's core body temperature being less than 36° C. (96.8° F.) or greater than 38° C. (100.4° F.) is not measured or considered in determining if the patient has two or more response criteria. In various embodiments, the criteria may be tested in any order.

At 120, a patient is tested to determine if the patient's WBC is <4,000 or >12,000 cells/mm$^3$. In various embodiments, the testing is specifically directed at determining if the patient's leukocytes are less than 4000 cells/mm$^3$ (4×109 cells/L) or greater than 12,000 cells/mm$^3$ (12×109 cells/L). In various embodiments, a patient will be considered to meet the response criterion if the patient's WBC is <5,000 or >12,000 cells/mm3. In various embodiments, the patient is not tested for the presence of greater than 10% immature neutrophils (band forms). In various embodiments, the testing method to determine the WBC may be any of the methods known in the art.

If the patient is found to not have a WBC outside the range of 4,000 to 12,000 cells/mm3, the patient may still be diagnosed with SIRS if the patient meets the two other response criteria.

In various embodiments, a patient that has a WBC<4,000 or >12,000 cells/mm3 is considered to meet that response criterion.

At 130, a patient that does not have a WBC outside the range of 4,000 to 12,000 cells/mm3 is tested to determine if the patient's heart rate is >90 BPM. If the patient's heart rate is >90 BPM, the patient will be considered to meet that response criterion. In various embodiments, a patient with a heart rate of >85 BPM will be considered to meet that response criterion. The testing method to determine the patient's heart rate may be any of the methods known in the art.

In various embodiments, a patient that has a WBC outside the range of 5,000 to 12,000 cells/mm3 is tested to determine if the patient's heart rate is >90 BPM. If the patient's heart rate is >90 BPM, the patient will be considered to meet that response criterion. In various embodiments, a patient with a heart rate of >85 BPM will be considered to meet that response criterion.

At 185, a patient that does not exhibit both a WBC<4,000 or >12,000 cells/mm3 and a heart rate that is >90 BPM is considered to not qualify for two of the three response criteria, and therefore does not meet the requirements to be treated with terlipressin. A patient failing to meet at least two of the three response criteria is excluded from the terlipressin treatment. Such a patient may be treated instead with one or more other pharmacological agents such as nor-epinephrine, vasopressin, or a combination of midodrine and octreotide. Alternatively or in addition, any of the following may be used: N-acetylcysteine, misoprostol, and/or BQ123. Another option is transjugular intrahepatic portosystemic shunt (TIPS). Renal support in the form of dialysis is commonly instituted to manage acute fluid overload in HRS-1 patients, particularly if pharmacological therapies fail. The only effective and permanent treatment for end-stage cirrhosis and HRS is liver transplantation.

At 140, a patient that has a WBC outside the range of 4,000 to 12,000 cells/mm3 or a heart rate that is >90 BPM is tested to determine if the patient has >20 breaths per minute or an HCO3<21 mmol/L. If the patient has >20 breaths per minute or an HCO3<21 mmol/L, the patient will be considered to meet that response criterion. In various embodiments, a patient with an HCO3<23 mmol/L will be considered to meet that response criterion. The testing method to determine the patient's breathing rate or HCO3 may be any of the methods known in the art.

In various embodiments, a patient that has a WBC outside the range of 5,000 to 12,000 cells/mm3 is tested to determine if the patient has a breathing rate that is >20 breaths per minute or an HCO3<21 mmol/L. If the patient has a breathing rate that is >20 breaths per minute or an HCO3<21 mmol/L, the patient will be considered to meet that response criterion. In various embodiments, a patient with an HCO3<23 mmol/L will be considered to meet that response criterion.

In one or more embodiments, if the patient has a WBC outside the range of 4,000 to 12,000 cells/mm3 and the patient has >20 breaths per minute or an HCO3<21 mmol/L, the patient is considered to qualify for two of the three response criteria, and therefore meets the requirements to be treated with terlipressin unless otherwise excluded.

In one or more embodiments, if the patient has a heart rate that is >90 BPM and the patient has a breathing rate that is >20 breaths per minute or an HCO3<21 mmol/L, the patient is considered to qualify for two of the three response criteria, and therefore meets the requirements to be treated with terlipressin unless otherwise excluded.

At 135, a patient that has a WBC outside the range of 4,000 to 12,000 cells/mm3, but does not have >20 breaths per minute or an HCO3<21 mmol/L, is tested to determine if the patient's heart rate is >90 BPM. If the patient's heart rate is >90 BPM, the patient will be considered to meet that response criterion. In various embodiments, a patient with a heart rate of >85 BPM will be considered to meet that response criterion.

In one or more embodiments, in which the patient has a WBC outside the range of 5,000 to 12,000 cells/mm3, but the patient does not have >20 breaths per minute or an HCO3<21 mmol/L, the patient is tested to determine if the patient's heart rate is >90 BPM. If the patient's heart rate is >90 BPM, the patient will be considered to meet that response criterion. In various embodiments, a patient with a heart rate of >85 BPM will be considered to meet that response criterion.

In one or more embodiments, if the patient has a breathing rate that is >20 breaths per minute or an HCO3<21 mmol/L a heart rate that is >90 BPM and the patient has a breathing rate that is >20 breaths per minute or an HCO3<21 mmol/L, the patient is considered to qualify for two of the three response criteria, and therefore meets the requirements to be treated with terlipressin unless otherwise excluded.

At 186, a patient that does not exhibit (1) a breathing rate that is >20 breaths per minute or an HCO3<21 mmol/L and does not exhibit (2) a heart rate that is >90 BPM is considered to not qualify for at least two of the three response criteria, and therefore does not meet the requirements to be treated with terlipressin. A patient failing to meet at least two of the three response criteria is excluded from the terlipressin treatment. Optional alternative treatments for such a patient are described above.

While the tests for the response criteria have be discussed in a particular order for the exemplary embodiment, the tests may be done in any particular order.

In one or more embodiments, temperature is not a response criterion because patient temperature may not provide an accurate indication of patient response to terlipressin. In various embodiments, patient temperatures are excluded from the set of response criteria.

At 150, a patient that has end stage liver disease with impaired renal function, and qualifies for at least two of the three response criteria, is started on terlipressin. In various embodiments, terlipressin is administered to the patient for one to four days. In various embodiments, the patient is administered terlipressin for four days unless the patient experiences an adverse event. In various embodiments, the terlipressin is administered to the patient as an IV drip.

In one or more embodiments, the terlipressin treatment protocol comprises administering a dosage of terlipressin in the range of about 0.1 mg to about 10 mg, or 0.5 mg to about 5.0 mg, or 0.5 mg to about 2.0 mg, or about 0.5 mg to about 1.0 mg, or about 1.0 mg to about 2.0 mg to the patient over about four hours to about six hours as an IV drip.

In one or more embodiments, the patient is administered terlipressin as an IV about every 4 to 6 hours for 1 to 4 days. In various embodiments, the terlipressin may be administered for at least 4 days.

In one or more embodiments, the patient is administered terlipressin as a slow bolus over 2 minutes about every 4 to 6 hours for 1 to 4 days. In various embodiments, the terlipressin may be administered for at least 4 days.

At 160, the patient that is being administered the terlipressin is tested at least once during the one to four day period of administration to determine if the patient is responding to the terlipressin. In various embodiments, the patient may be tested once prior to beginning the administration of the terlipressin to establish a baseline and once during the one to four days of terlipressin administration, or once prior to beginning the administration of the terlipressin to establish a baseline and once at the end of the four days of administration of the terlipressin. In various embodiments, the patient's creatinine levels are measured to determine if there has been a reduction in the patient's serum creatinine, where a reduction in serum creatinine levels of about 1.0 mg/dL or greater, or in the range of about 1.0 mg/dL to about 2.0 mg/dL, or a reduction of about 1.7 mg/dL from the patient's initial baseline value indicates an improvement in renal function and that the patient is responding to the terlipressin.

In various embodiments, improvement in renal function is indicted by a decrease in serum creatinine level of about 25% in the patient receiving terlipressin.

In one or more embodiments, a patient may have his or her serum creatinine levels measured once a day or once every other day for each of the four day period after administration of terlipressin has begun, wherein a measurement made on the first day of terlipressin administration may be recorded and used as the baseline creatinine level.

In various embodiments, the method may comprises testing the patient's SCr level during the 1 to 4 days of terlipressin administration and determining if the patient has a reduction in SCr level by the end of the 1 to 4 days of terlipressin administration.

The serum creatinine levels may be measured by any of the methods known in the art, for example, the Jaffe reaction using alkaline picrate.

The GFR may be measured directly by clearance studies of exogenous markers, such as inulin, iohexol, iothalamate, and Cr51-EDTA, or by estimated glomerular filtration rate (eGFR) using creatinine testing methods that are traceable to a reference method based on isotope dilution-mass spectrometry (IDMS).

At 170, a patient that shows a positive response to the administration of the terlipressin evidenced by a reduction in the patient's serum creatinine level is continued on the terlipressin at the dosage in the range of about 0.1 mg to about 10 mg, or 0.5 mg to about 5.0 mg, or 0.5 mg to about 2.0 mg, or about 0.5 mg to about 1.0 mg, or about 1.0 mg to about 2.0 mg. In various embodiments, the dosage administered to the patient may be adjusted based upon the measured serum creatinine level(s). In various embodiments, a patient being administered terlipressin may have their serum creatinine levels monitored for the entire time period that the patient is receiving terlipressin. In one or more embodiments, the patient's serum creatinine level may be tested every day, or every other day, or every third day, or every fourth day, to confirm that the patient is still responding positively to the terlipressin treatment.

In various embodiments, the patient's terlipressin dosage may be increased from about 0.5 mg to about 1.0 mg to about 1.0 mg to about 2.0 mg after 2-3 days of terlipressin administration to the patient if there is <1.5 mg/dL decrease in SCr during the first 2-3 days of treatment.

In various embodiments, the dosage may be repeated every four to six hours for a time period of one or more days until the patient shows recovery, or until the patient no longer shows improvement. The terlipressin may be administered to the patient for a time period in the range of about two days to about sixteen days, or for a time period in the range of about four days to about eight days. In various embodiments, the time period is in the range of about seven days. In various embodiments, the terlipressin treatment may be continued until there is a complete response. In various embodiments, the duration of treatment of a patient with terlipressin may be 1 to 28 days.

At 190, a patient that does not show any improvement by the end of four days may have the terlipressin discontinued, where improvement is indicated by a decrease in serum creatinine levels over the one to four days the terlipressin is administered. In various embodiments the patient may be tested on the third or fourth day after starting treatment with the terlipressin to determine if there is a decrease in serum creatinine levels indicating a response to the treatment.

In one or more embodiments, a patient is provided 2 days of anti-infective therapy for documented or suspected infection before starting administration of terlipressin if an infection is suspected. In various embodiments, a patient may be started on the terlipressin treatment protocol after the patient has been administered the anti-infective therapy.

Figure 2:
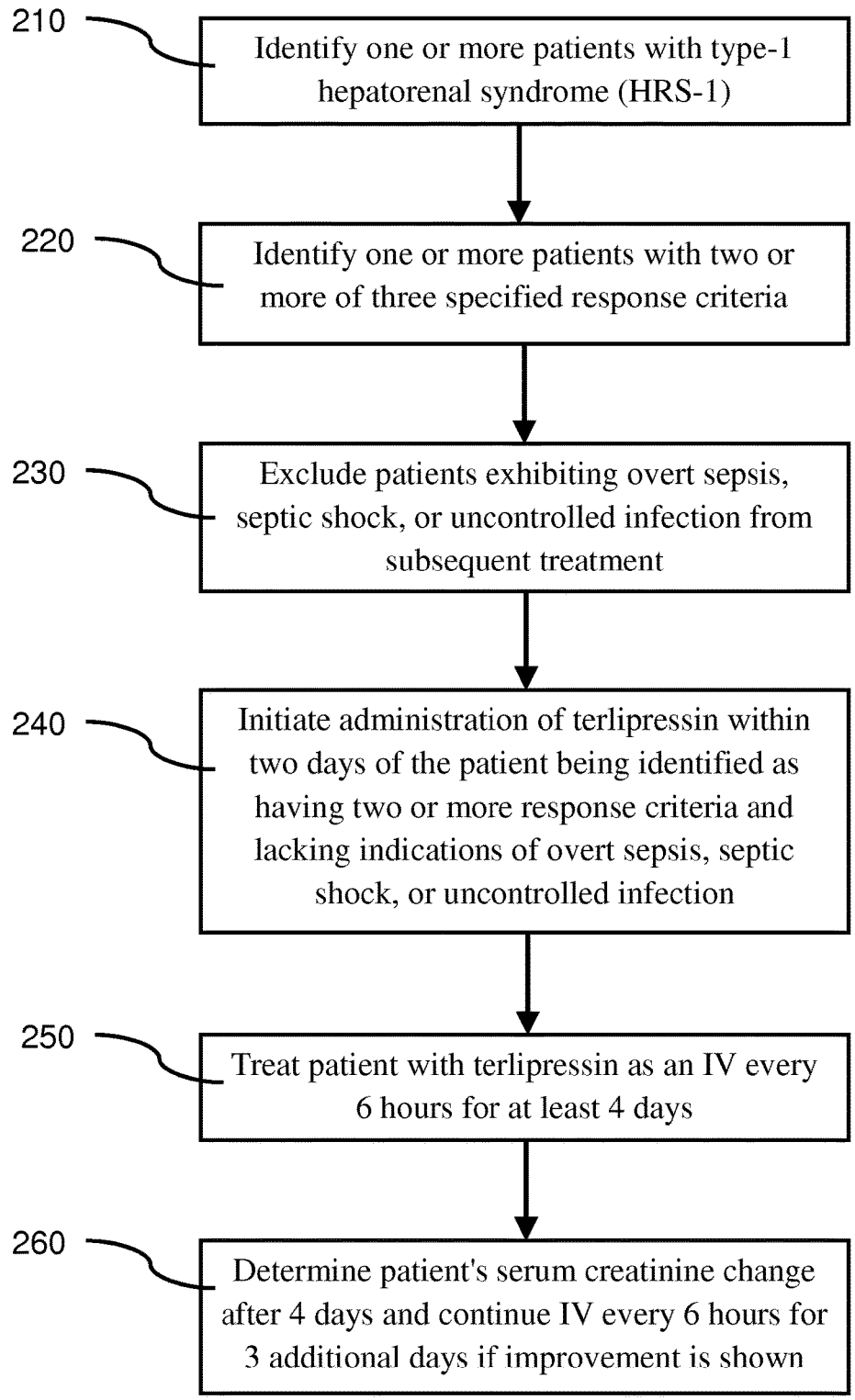
FIG. 2 illustrates an exemplary embodiment of a terlipressin treatment protocol.

FIG. 2 illustrates an exemplary embodiment of a terlipressin treatment protocol.

Principles and embodiments of the present disclosure also relate to providing terlipressin as an IV every four to six hours to patients that have been identified with HRS-1 and two or more of three specific response criteria.

In one or more embodiments, a patient is tested for (1) a white blood cell count (WBC)<4 or >12 cells/µL; (2) a heart rate (HR)>90 beats per minute (bpm), and (3) HCO3<21 mmol/L.

A non-SIRS patient is defined as subjects with <2 of the response criteria described above.

In various embodiments, temperature is not used as a response criteria.

In one or more embodiments of the disclosure, terlipressin is administered to patients presenting with a particular set of symptoms to mitigate the vasoconstriction in the kidneys, and improve renal function as indicated by a reduction in serum creatinine levels of about 1.7 mg/dL from initial baseline.

At 210, one or more patients that may be presenting with end-stage liver disease are tested to determine whether they are suffering from cirrhosis with ascites, and have serum levels of creatinine>133 µmol/l. A patient identified as having HRS is further tested and/or their medical history checked to determine if the initial serum levels of creatinine have doubled to greater than 226 µmol/l in less than 2 weeks indicating type 1 HRS.

Patients having HRS-1 and at least two of three response criteria have surprisingly shown improved response to terlipressin treatment compared to non-SIRS HRS-1 patients, as indicated by reversal of the HRS indications. The HRS indications may include serum creatinine levels.

At 220, once a patient has been identified as suffering from HRS-1, the patient is tested to determine is the same patient is exhibiting at least two out of three criteria indicating SIRS, wherein the three criteria include a (1) WBC<4 or >12 cells/µL; (2) HR>90 bpm, and (3) HCO3<21 mmol/L.

In various embodiments, patients not identified as exhibiting at least two of the three response criteria in addition HRS-1 are excluded from the terlipressin treatment protocol. Patients having HRS-1 and exhibiting at least two of the three response criteria have surprisingly shown improved response to terlipressin treatment compared to non-SIRS HRS-1 patients, as indicated by reversal of the HRS indications, as shown in FIG. 3.

At 230, patients that have been identified as having HRS-1 and exhibit at least two response criteria are tested to determine if they may also have an uncontrolled infection, sepsis, or septic shock, wherein patients identified as exhibiting an uncontrolled infection, sepsis, or septic shock are excluded from the terlipressin treatment protocol.

At 240, patients that have HRS-1, have at least two of the three response criteria, and do not have an uncontrolled infection, sepsis, or septic shock are started on the terlipressin treatment. In one or more embodiments, the terlipressin treatment is started within 48 hours of the initial diagnosis that the patient has both HRS-1 and at least two of three response criteria. In various embodiments, in which the determination that the patient does or does not also have an uncontrolled infection, sepsis, or septic shock occurs after 48 hours of the initial diagnosis of both HRS-1 and the response criteria, the treatment protocol is started within 48 hours of the initial diagnosis, and treatment may be terminated once an uncontrolled infection, sepsis, or septic shock manifests or is determined.

In various embodiments, a baseline serum creatinine level may be determined for the patient prior to starting the administration of terlipressin to the patient; and the administration of terlipressin started within 2 days or within 3 days, or within 4 days of determining the baseline serum creatinine level. In various embodiments, the patient may be tested at least once daily within four days after starting the administration of terlipressin to determine if the patient exhibits a decrease in the serum creatinine level compared to the previously determined baseline serum creatinine level.

At 250, terlipressin treatment of the patient is started and the patient receives a dosage of terlipressin. In one or more embodiments, the terlipressin may be administered to a patient as a slow infusion over 24 hours, wherein the dosage over the 24 hour period may be in the range of about 2.0 mg to about 12 mg. In various embodiments, the dosage over the 24 hour period may be in the range of about 2.0 mg to about 4.0 mg. In various embodiments, the terlipressin is administered as a continuous intravenous (IV) drip lasting from about 4 hours to about 6 hours, and comprising a dosage of about 0.5 mg to about 2.0 mg.

In one or more embodiments, the terlipressin dosage may be a dosage of about 0.5 mg to about 2.0 mg administered intravenously every 4 to 6 hours as a slow bolus injection over 2 minutes.

In one or more embodiments, the terlipressin is used to treat the patient exhibiting HRS-1 and at least two of the three response criteria. In various embodiments, the patient is also tested to determine that the patient does not have an uncontrolled infection, sepsis, or septic shock before being using the terlipressin to treat the HRS-1 patient.

In various embodiments, the terlipressin dosage is given as a continuous IV feed.

In one or more embodiments, the terlipressin dosage is 1 mg administered intravenously every 6 hours as a slow bolus injection over 2 minutes.

In various embodiments, the terlipressin dosage is not given as a bolus.

The terlipressin may be administered to the patient for up to 4 days, wherein the patient may be tested each day of the four days to determine whether the patient is responding to the terlipressin treatment. In various embodiments, a response to the terlipressin treatment may be indicated by a change in the patient's serum creatinine levels, where indication may be a reduction in SCr of at least 25% from baseline. In various embodiments, the terlipressin may be administered for at least 4 days.

At 260, the amount of serum creatinine change is determined after 4 days of treatment with terlipressin, and the treatment with terlipressin continued if the serum creatinine level has improved. In various embodiments, a sufficient improvement in serum creatinine levels after 4 days of treatment is indicated by a decrease of at least 1.0 mg/dL in serum creatinine level, or a decrease of about 1.7 mg/dL in serum creatinine level.

In various embodiments, the patient receives terlipressin for an additional 3 days to 8 days if improvement was exhibited over the previous 1 to 4 days. In various embodiments, the patient receives terlipressin for an additional 3 days to 4 days if improvement was exhibited over the previous 1 to 4 days.

In various embodiments, the administration of terlipressin to the patient is continued for an additional 3 days to 12 days beyond the initial 4 days if the patient exhibits a decrease in the serum creatinine level. In various embodiments, administration of terlipressin to the patient may be continued until at least one SCr value<1.5 mg/dL is obtained. In various embodiments, the duration of treatment may be extend to a maximum of 15 days or 16 days if HRS reversal was first achieved on days 13 or 14, respectively. In various embodiments, the duration of treatment of a patient with terlipressin may be 1 to 28 days. In various embodiments, a decrease in the serum creatinine level may be indicated by a reduction in SCr of at least 1% or of at least 5% or at least 10% or at least 15% or at least 20% or at least 25% from baseline.

[00120] In one or more embodiments, the patient may have been administered albumin prior to beginning the terlipressin treatment protocol, and/or prior to the determination that the patient has HRS-1, at least two of the three response criteria. In various embodiments, albumin may be administered to a patient 7 days to 2 days before starting administration of terlipressin to the patient. In various embodiments, the albumin treatment comprises administering 1 gram albumin per 1 kg of patient weight up to a maximum of 100 g per day of albumin to a patient. In various embodiments, albumin may be administered in the range of about 20 g/day to about 50 g/day, where the albumin may be administered for the time period that the patient is administered terlipressin.

A non-limiting embodiment of a method of treating HRS-1 patients exhibiting at least two of three response criteria with terlipressin comprises administering to a patient in need of such treatment a dosage of terlipressin in the range of 2.0 mg to 12.0 mg per day for 1 to 28 days, or in the range of 2.0 mg to 4.0 mg per day for 1 to 7 days, wherein the dosage may be administered as a continuous IV feed or as a slow bolus injection.

Embodiments of the present disclosure also relate to treating patients with HRS-1 and meeting two or more response criteria with one dose of terlipressin every six hours, where the dose is in the range of about 0.5 mg to 2.0 mg, for 3 to 8 days to achieve reversal of the HRS-1.

Embodiments of the present disclosure also relate to initiating terlipressin treatment within 48 hours of determining that a patient is presenting with HRS-1 and at least two of three response criteria, but without sepsis, septic shock, or uncontrolled infection.

Another aspect of the present disclosure relates to a method of distributing a pharmaceutical product.

In one or more embodiments, the method of distributing comprises supplying terlipressin to a medical provider, where the medical provider may be responsible for treating a patient suffering from type 1 hepatorenal syndrome. In various embodiments, the patient does not have overt sepsis, septic shock, or uncontrolled infection. In various embodiments, the method includes providing a recommendation to the medical provider to treat the patient suffering from type 1 hepatorenal syndrome that does not have overt sepsis, septic shock, or uncontrolled infection and having at least two of (1) a white blood cell count (WBC) is less than 4,000 cells/mm$^3$ or greater than 12,000 cells/mm$^3$, (2) a heart rate of greater than 90 beats per minute (BPM), or (3) an HCO3<21 mmol/L, with terlipressin in an amount effective to reduce SCr. In one or more embodiments, the medical provider follow the recommendation and administers a treatment to the patient suffering from HRS-1, but not overt sepsis, septic shock, or uncontrolled infection and having at least two of (1) a white blood cell count (WBC) is less than 4,000 cells/mm$^3$ or greater than 12,000 cells/mm$^3$, (2) a heart rate of greater than 90 beats per minute (BPM), or (3) an HCO3<21 mmol/L, with terlipressin in an amount effective to reduce SCr.

FIG. 3 shows the unexpected results produced by an exemplary treatment protocol.

A randomized, placebo-controlled, double-blind study was conducted to evaluate the efficacy of terlipressin in HRS type 1. The objective of the study was to determine the efficacy and safety of intravenous terlipressin compared with placebo in the treatment of adult patients with HRS type1 receiving intravenous albumin. Men and women aged 18 years or older having cirrhosis, ascites, and a diagnosis of HRS type 1 based on the 2007 International Ascites Club (IAC) diagnostic criteria (Salerno F, Gerbes A, Gines P, Wong F, Arroyo V., Diagnosis, prevention and treatment of hepatorenal syndrome in cirrhosis, Gut. 2007; 56:1310-1318) were eligible for participation. Patients with an SCr level>2.5 mg/dL and either a doubling of SCr within 2 weeks or a change in SCr levels over time indicating a trajectory with a slope equal to or greater than that of a doubling within 2 weeks were enrolled.

Exclusion criteria were intended to product a patient sample limited to individuals with functional renal impairment secondary to cirrhosis and ascites, who could safely be administered terlipressin and who could be expected to survive through the active study period. Among the original exclusion criteria was an exclusion criterion for patients with systemic inflammatory response syndrome (SIRS), defined as the presence of 2 or more of the following findings: (1) temperature>38° C. or <36° C.; (2) heart rate>90/min; (3) respiratory rate of >20/min or a PaCO2 of <32 mm Hg; (4) white blood cell count of >12,000 cells/μL or <4,000/μL. This was based on the concern of enrolling patients with uncontrolled infection. However, it was also recognized that patients with decompensated liver disease frequently have SIRS criteria in the absence of uncontrolled infection or sepsis, and that the presence of 2 or more SIRS criteria is associated with a poor prognosis (Thabut, et al., "Model for End-Stage Liver Disease Score and Systemic Inflammatory Response Are Major Prognostic Factors in Patients with Cirrhosis and Acute Functional Renal Failure," HEPATOLOGY, Vol. 46, No. 6, December 2007, pp. 1872-1882). Furthermore, the IAC criteria for the definition of HRS type 1 allows for patients with ongoing bacterial infection, but not sepsis or uncontrolled infection, to be considered as having HRS type 1 (as opposed to renal dysfunction associated with infection) (Salerno F, Gerbes A, Gines P, Wong F, Arroyo V., Diagnosis, prevention and treatment of hepatorenal syndrome in cirrhosis, Gut. 2007; 56:1310-1318). The trial protocol required 2 days of anti-infective therapy for documented or suspected infection, allowing enrollment where any SIRS criteria were felt to be most likely explained by underlying hepatic decompensation or other non-infection clinical circumstances. This approach was felt to minimize the chances of enrolling patients at high risk for serious infection while not unduly restricting the enrollment of subjects with HRS type 1.

The patients selected for treatment clinically met the criteria for HRS type 1, where IAC criteria for HRS type 1 allows for patients with ongoing bacterial infection, but not sepsis, to be considered as having HRS type 1, as opposed to renal dysfunction associated with infection. A diagnosis of HRS was not made where the patient remained with obvious manifestations of uncontrolled infection despite antibiotic treatment.

During the active study period treatment with the blinded study drug continued until at least two SCr values<1.5 mg/dL were obtained at least 48 hours apart, or up to 14 days. Duration of treatment was allowed to extend to a maximum of 15 or 16 days if HRS reversal was first achieved on days 13 or 14, respectively. Patients in the active treatment group received terlipressin 1 mg intravenously every 6 hours as a slow bolus injection over 2 minutes. Criteria for dose increases, study discontinuation, treatment resumption and treatment completion during the active study period were provided for. The dosing regimen for patients in the placebo (6 mL lyophilized mannitol solution) group was identical to the terlipressin regimen. The follow-up period began after the end of study treatment and concluded 90 days after the start of study treatment. Survival, renal replacement therapy, and transplantation were assessed.

The SIRS subgroup of patients in this study was defined as any subject with ≥2 of 3 criteria available from the study database which included: (1) WBC<4 or >12 cells/μL; (2) HR>90 bpm and (3) HCO3<21 mmol/L. The latter criterion represented an approximation of the SIRS criterion PaCO2 of <32 mm Hg. This approximation was derived from the observed HCO3 in subjects with HRS in whom a PaCO2 value was available and the calculated HCO3 in subjects with decompensated liver disease and PaCO2 of <32 mm Hg. The non-SIRS subgroup was defined as subjects with <2 criteria described above. Terlipressin response was analyzed in the SIRS and non-SIRS subgroups to determine whether SIRS status had any effect on terlipressin efficacy.

A total of 196 patients were enrolled in the study. Of the 196 patients enrolled, 58 were initially identified as having ≥2 SIRS criteria, including WBC<4 or >12 cells/μL, HR>90 bpm, and HCO3<21 mmol/L, wherein this population was identified as the SIRS subgroup. Based on the criteria defining the SIRS subgroup, baseline WBC and heart rate were slightly higher, and bicarbonate slightly lower, in the SIRS subgroup compared to the non-SIRS and overall study populations. The results of the analysis are shown in FIG. 3.

It was also recognized that patients with decompensated liver disease frequently have SIRS criteria in the absence of uncontrolled infection or sepsis, and that the presence of two or more SIRS criteria is associated with a poor prognosis.

In one or more embodiments, reversal of HRS is indicated by a decrease in SCr level to ≤1.5 mg/dl, and confirmed reversal of HRS is defined as two SCr values of ≤1.5 mg/dL at least 48 hours apart.

As shown in FIG. 3, patients identified as having HRS-1 and at least two of the three criteria for SIRS on a terlipressin treatment protocol exhibited a statistically significant increase in confirmed reversal of HRS (32.1% vs. 3.3%, p<0.005), HRS reversal (42.9% vs. 6.7%, p<0.002) and renal function (change from baseline in SCr, mg/dL, −1.7 vs. −0.5, p<0.0001) compared to placebo. In contrast, in the group of patients having HRS-1 and fewer than two of the SIRS criteria, confirmed reversal of HRS vs. placebo was 14.5% vs. 17.4%, HRS reversal vs. placebo was 15.9% vs. 18.8%, and renal function change vs. placebo was −0.8 vs. −0.7 mg/dL. These results indicate that the presence of two or more of the SIRS criteria indicates that the patient is more likely to have a positive response to treatment with terlipressin.

In addition, in the treatment groups, patients with HRS-1 and two or more SIRS criteria showed an overall survival rate comparable to patients that were suffering from HRS-1, but did not have at least two of the three criteria for SIRS (57.1% vs. 58%).

Although the disclosure herein has been described with reference to particular embodiments, it is to be understood that these embodiments are merely illustrative of the principles and applications of the present disclosure. It will be apparent to those skilled in the art that various modifications and variations can be made to the devices, systems, and methods of the present disclosure without departing from the spirit and scope of the disclosure. Thus, it is intended that the present disclosure include modifications and variations that are within the scope of the appended claims and their equivalents.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

What is claimed is:

1. A method of treating type 1 hepatorenal syndrome (HRS-1), the method comprising:
   identifying a plurality of patients as having HRS-1;
   determining that a first patient of the plurality exhibits at least two of the following three criteria for Systemic Inflammatory Response Syndrome (SIRS):
   (i) a white blood cell count (WBC) less than 4,000 cells/mm$^3$ or greater than 12,000 cells/mm$^3$,
   (ii) a heart rate of greater than 90 beats per minute (BPM), and
   (iii) either a partial pressure of carbon dioxide in the blood (PaCO$_2$)<32 mmHg or a blood bicarbonate (HCO$_3$) level<23 mmol/L;
   determining that the first patient does not have overt sepsis, septic shock, or uncontrolled infection;
   determining that, because the first patient exhibits at least two of the three criteria and does not have overt sepsis, septic shock, or uncontrolled infection, the HRS-1 of the first patient is likely to respond to treatment with terlipressin;
   administering to the first patient an amount of terlipressin effective to treat HRS-1 in the first patient;
   determining that a second patient of the plurality exhibits only one or none of the three criteria or has overt sepsis, septic shock, or uncontrolled infection;
   determining that, because the second patient does not exhibit at least two of the three criteria or has overt sepsis, septic shock, or uncontrolled infection, the HRS-1 of the second patient is unlikely to respond to treatment with terlipressin;
   excluding the second patient from treatment with terlipressin determining that a third patient of the plurality has overt sepsis, septic shock, or uncontrolled infection; and
   excluding the third patient from treatment with terlipressin.

2. The method of claim 1, wherein a treatment other than terlipressin is administered to the second patient.

3. The method of claim 1, wherein criterion (iii) is a HCO3 level<23 mmol/L.

4. The method of claim 1, wherein criterion (iii) is a HCO3 level<21 mmol/L.

5. The method of claim 1, wherein the amount of terlipressin administered to the first patient is in the range of 2.0 mg to 12.0 mg per day for 1 to 28 days.

6. The method of claim 5, wherein the amount of terlipressin administered to the first patient is in the range of about 0.5 mg to about 2.0 mg every 4 to 6 hours.

7. The method of claim 1, comprising determining if the first patient has a reduction in serum creatinine level during the initial 1 to 4 days of terlipressin administration.

8. The method of claim 7, comprising discontinuing administration of terlipressin to the first patient if the first patient does not show a reduction in serum creatinine level during the initial 1 to 4 days of terlipressin administration.

9. The method of claim 7, comprising continuing administration of terlipressin to the first patient for an additional 3 to 12 days if the first patient shows a reduction in serum creatinine level during the initial 1 to 4 days of terlipressin administration.

10. The method of claim 1, wherein administration of terlipressin to the first patient produces a decrease in serum creatinine level to ≤1.5 mg/dl.

11. The method of claim 1, comprising treating the first patient with up to a maximum of 100 g per day of albumin for each day of the time period that the first patient is administered terlipressin.

12. The method of claim 1, wherein administering terlipressin to the first patient provides reversal of one or more complicating factors.

13. The method of claim 12, wherein one or more of the complicating factors is splanchnic vasodilation.

14. The method of claim 12, wherein reversal of one or more complicating factors reduces mortality from an associated complication within a 90 day window starting with administering the terlipressin.

15. A method of increasing the effectiveness of terlipressin for the treatment of impaired renal function associated with liver disease, comprising:
   identifying a plurality of patients with end-stage liver disease and impaired renal function;
   testing the plurality of patients to determine whether each meets each of the following three criteria (i)-(iii):
   (i) a white blood cell count either less than 4,000 cells/mm$^3$ or greater than 12,000 cells/mm$^3$,
   (ii) a heart rate of greater than 90 beats per minute, and
   (iii) either (a) a partial pressure of carbon dioxide in the blood (PaCO$_2$) of <32 mmHg or (b) a blood bicarbonate HCO₃ level of <23 mmol/L or (c) tachypnea with more than 20 breaths per minute;

determining that a first patient of the plurality meets at least two of the three criteria;

determining that the first patient does not have overt sepsis, septic shock, or uncontrolled infection;

determining that, because the first patient meets at least two of the three criteria and does not have overt sepsis, septic shock, or uncontrolled infection, the first patient's renal function is more likely to improve upon treatment with terlipressin than if the first patient exhibited only one or none of the three criteria;

administering to the first patient an amount of terlipressin effective to improve the first patient's renal function;

determining that a second patient of the plurality meets only one or none of the three criteria or has overt sepsis, septic shock, or uncontrolled infection;

determining that, because the second patient does not meet at least two of the three criteria or has overt sepsis, septic shock, or uncontrolled infection, the second patient's renal function is less likely to respond to treatment with terlipressin than if the second patient exhibited at least two of the three criteria; and excluding the second patient from treatment with terlipressin.

16. The method of claim 15, wherein, during treatment with terlipressin, the first patient is tested to determine if the first patient's renal function is improved compared to prior to treatment with terlipressin.

17. The method of claim 15, wherein a treatment other than terlipressin is administered to the second patient.

18. The method of claim 15, wherein criterion (iii) is a HCO3 level<23 mmol/L.

19. The method of claim 15, wherein criterion (iii) is a HCO3 level<21 mmol/L.

20. The method of claim 15, comprising determining that a third patient of the plurality has overt sepsis, septic shock, or uncontrolled infection, and excluding the third patient from treatment with terlipressin because of the presence of overt sepsis, septic shock, or uncontrolled infection.

21. The method of claim 15, comprising determining that the plurality of patients have cirrhosis of the liver with a Child-Pugh score of B or C.

22. The method of claim 15, wherein the dosage of terlipressin administered to the first patient over a 4 hour to 6 hour period is in the range of about 0.5 mg to about 2.0 mg.

23. The method of claim 15, wherein the terlipressin is administered to the first patient as a continuous IV drip.

24. The method of claim 15, wherein the dosage of terlipressin administered to the first patient does not exceed 4.0 mg over each 24 hour period of administration.

25. The method of claim 15, comprising determining a baseline serum creatinine level for the first patient within 2 days prior to starting the administration of terlipressin to the first patient and testing the first patient at least once within four days after starting the administration of terlipressin to determine if the first patient's serum creatinine level has decreased compared to the baseline level.

26. The method of claim 25, wherein the administration of terlipressin to the first patient is continued if testing the first patient's serum creatinine level after starting the administration of terlipressin shows that the first patient's serum creatinine level has decreased compared to the baseline level, and the administration is discontinued if the first patient's serum creatinine level has not decreased compared to the baseline level.

27. The method of claim 26, wherein the first patient's serum creatinine level is shown to have decreased compared to the baseline level, and then administration of terlipressin to the first patient is continued for an additional 3 days to 8 days.

28. The method of claim 15, wherein, following treatment with terlipressin, the first patient's serum creatinine level is tested and found to be ≤1.5 mg/dl.

* * * * *